Figure 1:
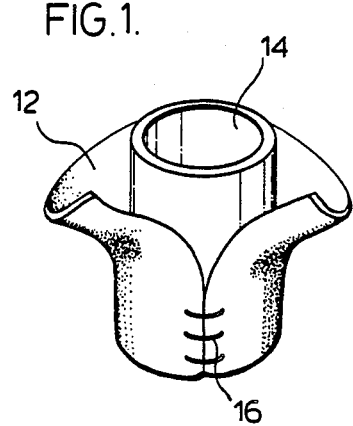

United States Patent [19]

Ovil

[11] Patent Number: 4,790,844
[45] Date of Patent: Dec. 13, 1988

[54] REPLACEMENT OF CARDIAC VALVES IN HEART SURGERY

[76] Inventor: Yoel Ovil, 33 Bainbridge Avenue, Downsview, Ontario, Canada, M3H 2J8

[21] Appl. No.: 8,816

[22] Filed: Jan. 30, 1987

[51] Int. Cl.[4] .............................................. A61F 2/24
[52] U.S. Cl. ....................................................... 623/2
[58] Field of Search ............................................ 623/2

[56] References Cited

U.S. PATENT DOCUMENTS 4,274,437 6/1981 Watts ...................................... 623/2
4,624,822 11/1986 Arro et al. ............................. 623/2
4,626,255 12/1986 Reichart .................................. 623/2
4,629,459 12/1986 Iouescu .................................... 623/2

OTHER PUBLICATIONS

"The Autologous Rectus Sheath Cardiac Valve", Athanasuleas et al., *The Journal of Thoracic & Cardiovascular Surgery* vol. 65, No. 1, pp. 118–123, Jan. 1973.

*Primary Examiner*—Richard J. Apley
*Assistant Examiner*—James Prizant

[57] ABSTRACT

A cardiac valve has an annular body of unsupported natural or artificial tissue. The annular body has a bishop's miter shape with a cylindrical end and a pair of diametrically-opposite triangular flap portions extending therefrom. Each flap portion has a free apical end.

7 Claims, 3 Drawing Sheets

REPLACEMENT OF CARDIAC VALVES IN HEART SURGERY

This invention relates to cardiac valve replacement in heart surgery.

Cardiac valve replacement is nowadays a relatively common procedure. However, replacement cardiac valves which are used in known procedures are either mechanical or of bioprosthetic construction, usually comprising a tissue-covered rigid frame, the tissue being for example surgical pig tissue. Patients receiving mechanical valves require anticoagulant therapy and run the risk of the occurrence of thromboembolic phenomena. Although the likelihood of such problems is substantially reduced with bioprosthetic instructions such as tissue-covered rigid frame valves, such valves do not have an adequately long life, with re-operation consequently being necessary in due course. Also, both mechanical and bioprosthetic valves may cause a reduction in proper least function due to the rigidity of the structure and lack of support to the papillary muscles or in the side walls of the pulmonary artery or the aorta as the case may be.

It is therefore an object of the present invention to provide an improved cardiac valve and replacement procedure therefor.

According to the present invention, cardiac valve replacement procedure utilizes natural or artificial tissue without any supporting structure. The natural tissue may be suitable tissue from the patient or from another human or an animal, and the artificial tissue may be for example suitable synthetic plastic material or bioengineered tissue produced from human or animal tissue.

The present invention provides a cardiac valve having an annular body of unsupported natural or artificial tissue, the annular body having a bishop's miter shape with a cylindrical end and a pair of diametrically-opposite triangular flap portions standing therefrom, each flap portion having a full apical end. To produce such a valve, a rectangular piece of tissue may be provided and formed into a cylinder by securing opposed end edges of the rectangular piece of tissue together, preferably with the assistance of a cylindrical former around which the tissue is wound. Two diametrically-opposite triangular portions are then removed to create the bishop's miter shape with a cylindrical end and a pair of diametrically-opposite flap portions extending therefrom, each flap portion having a free apical end. Such a cardiac valve can be manufactured and supplied ready for use in sterile packaging.

If suitable synthetic plastic material is used, it may be structured as a cylinder which is subsequently cut to the required length. Diametrically-opposite portions are then removed to create the biship's miter shape.

During surgery, and after the usual preparation of the patient and removal of a defective cardiac valve, the cylindrical (unmitered) end of the replacement valve is secured to the native annulus. Each flap portion is secured to papillary muscle or to the side wall of the pulmonary artery or the aorta, as the case may be, by temporarily securing opposite side edges of an upper part of the flap portion to the annulus at diametrically opposite positions to close that half of the annulus, securing the apical end of the flap portion to papillary muscle or side wall, and releasing the upper part of the flap portion from the annulus. The temporary securements represent the commissures of the new valve.

Alternatively, the tissue may be endocardium of the patient's own heart. In this case, an appropriate annular portion of endocardium is partially detached by a circular cut around the annulus. Thus, a tissue cylinder already attached at one end to the annulus is provided. Two diametrically-opposite triangular portions are then removed from the opposite end, and attachment of the diametricallyopposite flap portions thereby formed to papillary muscle or side wall is effected in the same manner as previously described.

It will therefore be clear that use of the present invention substantially reduces or obviates the disadvantages of known procedures in which mechanical or tissue-covered rigid frame prosthetic valves are used.

Figure 2:
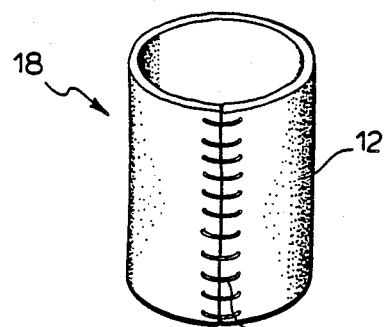
Figure 3:
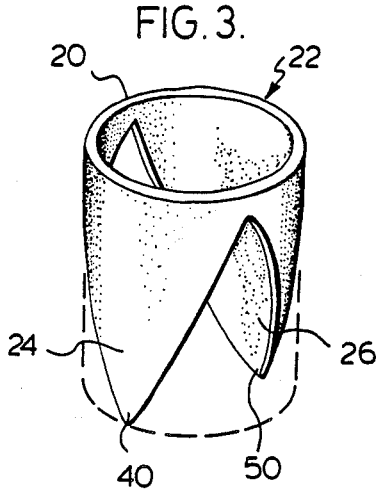
Figure 4:
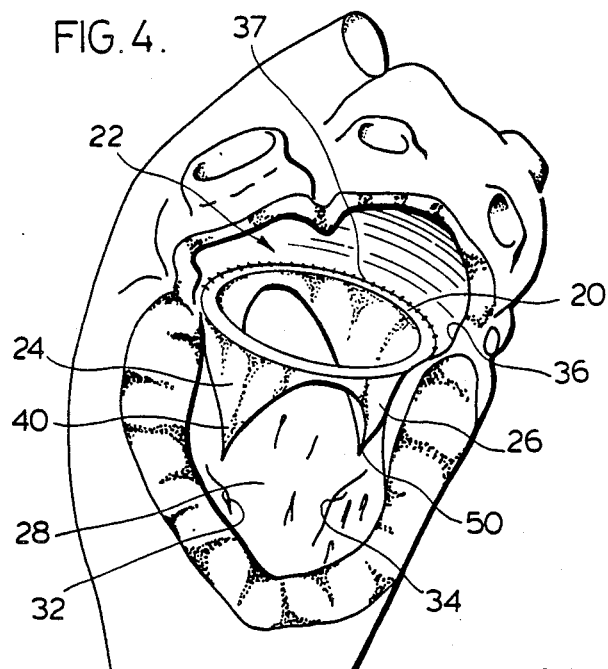
Figure 5:
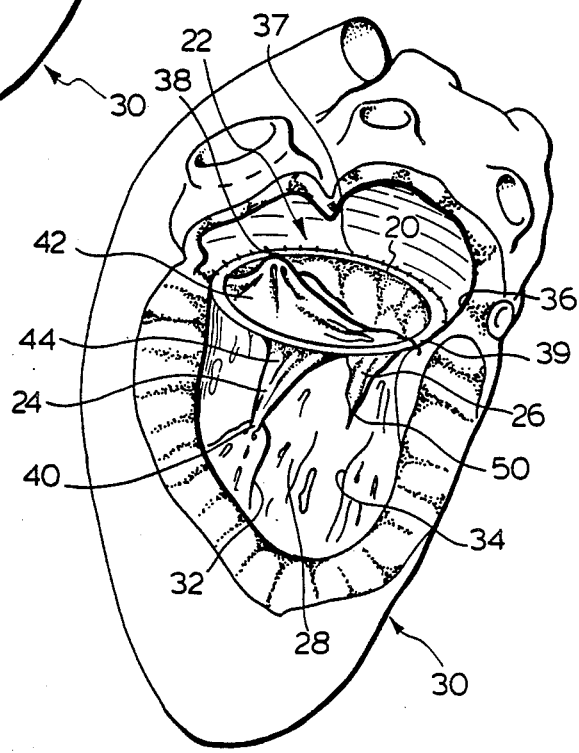
Figure 6:
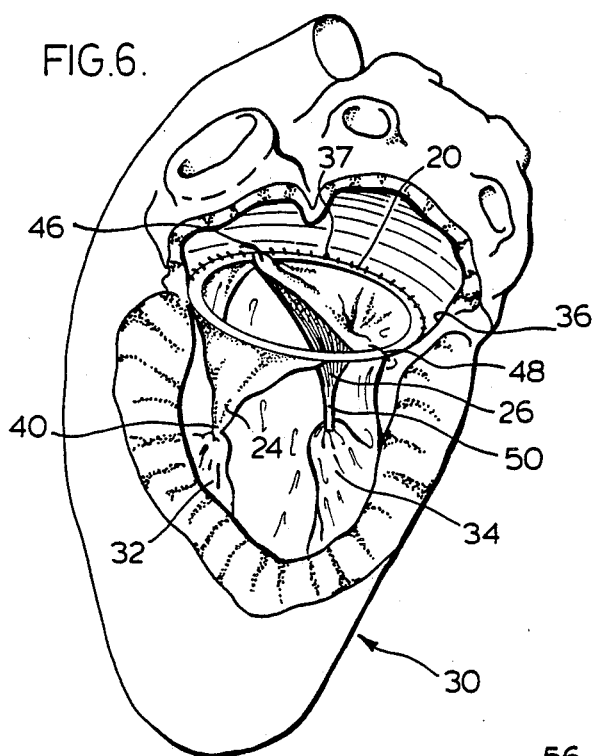
Figure 7:
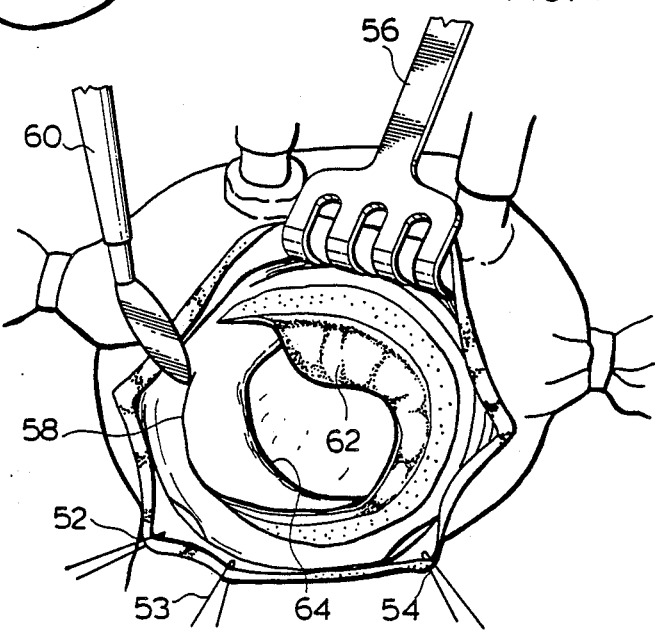

Embodiments of the invention will now be described, by way of example, with reference to the accompanying drawings, of which:

FIG. 1 is a perspective view of an initial step in the formation of a tissue valve cylinder using a portion of the patient's own pericardium in accordance with one embodiment of the invention, FIG. 2 is a similar view showing completion of the tissue valve cylinder, FIG. 3 is a similar view after removal of diametrically-opposite triangular portions to form the valve into a shape of a bishop's miter, FIG. 4 is a similar view showing an initial step in securing the valve to a left ventricle, namely securing the non-mitered end to the ventricle annulus, FIG. 5 is a similar view showing the securing of the apical end of one of the flap portions to papillary muscle, FIG. 6 is a similar view showing the securing of the other flap portion to the papillary muscle, and FIG. 7 is a prospective view of an initial step in the formation of a tissue valve using the patient's own endocardium in accordance with another embodiment of the invention.

Referring first to FIGS. 1 to 6 of the accompanying drawings, heart surgery on the patient is commenced in a conventional manner. After midline sternotomy, a rectangular piece of pericardium 12 is excised. The excised pericardium 12 is then wound around a form 14 in the form of a plastic cylinder, as shown in FIG. 1, and the opposite end edges of the excised pericardium 12 are secured together by sutures 16. The former 14 is then removed, thereby leaving a tissue valve cylinder 18. Two diametrically-opposed portions are then removed by appropriate cutting from one end of the valve cylinder 18 to create a bishop's miter shape, as shown in FIG. 3, with the tissue valve 22 thus formed having a cylindrical end 20 from which two diametrically-opposite flap portions 24, 26 project. The flap portions 24, 26 each have a free apical end 40, 50 respectively.

The patient's heart is prepared in a suitable manner, for example by double cannulation which is standard for mitral valve surgery, cardiac arrest by cardioplegia and topical hypothermia with exposure of the left atrium by a longitudinal incision posterior to the inner atrial groove. The diseased valve is excised 3 to 4 mm from the ventricle annulus and at the point of incerstion of the chordae tendineae to the papillary muscles.

The newly formed valve 22 is then inserted into the left ventricle 28 of the patient's heart 30, with the triangular flap portions 24, 26 directed towards papillary muscles 32, 34 respectively as shown in FIG. 4. The cylindrical end 20 of the valve 22 is then secured to the ventricle annulus 36 by sutures 37, with suitable suture material being for example running 3-0 prolene.

To attach the triangular flap portion 26 to the papillary muscle 32, the upper part of the flap portion 24 is pulled up inwardly and its opposite side edges temporarily secured to diametrically-opposite positions on the annulus 28 by temporary stay sutures 38, 39, so as to close half of the mitral orifice with the upper part of the flap portion 24. The temporary stay sutures 38, 39 represents the commissures of the new valve.

The apical end 40 of the flap portion 24 is then secured under tension to the papillary muscle 32 as indicated in FIG. 5. This is achieved by making a small cut (not shown) in the apex of the papillary muscle, inserting the apical end 40 of the flap portion 24 between the two lips of the cut, and securing the apical end 40 therein by a plegetted suture.

The valve flap 24 therefore now has two anchored parts, namely a horizontal part 42 extending from half the periphery of the annulus 28 to the diameter defined by the temporary stay sutures 38, 39, and a vertical part 44 extending from the defined diameter downwardly to the papillary muscle 32, both of these parts being under tension. The two stay sutures 38, 39 are then released to allow the two parts 42, 44 of the valve portion 24 to fall freely into the left ventricular cavity 28 as indicated in FIG. 6.

The same procedure which was followed with flap portion 24 is then repeated with flap portion 26, namely by first inserting stay sutures 46, 48 at exactly the same positions on the annulus 36 as stay sutures 38, 39 were provided, and then securing the apical end 50 of flap portion 26 to the papillary muscle 34, the sutures 46, 48 thereafter being released.

The new mitral valve is then checked for regurgitation by injection of saline into the left ventricle through the newly formed valve from the atrial side.

In the above-described embodiment, the valve was formed from the patient's own pericardium. It will readily be apparent to a person skilled in the art that the valve could also be formed from any other suitable human or animal tissue or from suitable artificial material such as a suitable synthetic plastic material or bioengineered tissue produced from human or animal tissue. Such cardiac valves can be manufactured and supplied ready for use in sterile packaging.

Referring now to FIG. 7, a valve in accordance with the present invention can be formed from the patient's own endocardium, and in this case the endocardial material does not have to be completely detached from the patient's heart. Under the usual conditions of cardiopulmonary by-pass and cardioplegic arrest with left atrial exposure, the left atrium is opened at the level of the right superior pulmonary vein, continuing to the upper part of the right inferior pulmonary vein.

In accordance with the invention, as shown in FIG. 7, three stay sutures 52, 53, 54 are inserted on one side of the atrium opening, with the other side being held by a retractor 56. The diseased valve is then excised as in the previous embodiment.

A circular and shallow incision 58, incising only the endocardium, is made by a scapel 60, beginning at the posterior wall of the left atrium just below the entry of the inferior pulmonary vein, and continuing to the inter atrial septum rising anteriorally during its course. The endocardial cylinder 62 so formed is pulled upwardly from the cut 58 towards the annulus 64, with which one end of the endocardial cylinder 62 is accordingly integral.

A procedure similar to the procedure of the previous embodiment is then followed, namely by removing two diametrically-opposite triangular portions from the opposite end of the endocardial cylinder 62 to create a bishop's miter shape with two diametrically-opposite triangular flap portions which, after being inverted, are attached at their apical ends to papillary muscle in the same manner as previously described.

An advantage of this embodiment is of course that the mitral valve constructed from the patient's own endocardium has an in situ attachment to the heart wall, has its own source of oxygenated blood supply and has an endothelial surface.

Other embodiments of the invention will be readily apparent to a person skilled in the art, the scope of the invention being defined in the appended claims.

What I claim as new and desire to protect by Letters Patent of the United States is:

1. A cardiac valve having an annular body of flexible unsupported natural or artifical tissue, said annular body having a bishop's miter shape with a cylindrical end portion and a pair of diametrically-opposite triangular flexible flap portions integral with and extending from the cylindrical end portion, each flexible flap portion having a free apical end.

2. A cardiac valve according to claim 1 wherein the annular body is of animal pericardium.

3. A cardiac valve according to claim 2 wherein the pericardium is bovine or pig pericardium.

4. A method of replacing a cardiac valve in a heart of a patient;
the method comprising providing a tissue valve consisting of flexible unsupported natural or artifical tissue having a bishop's miter shape with a cylindrical end portion and a pair of diametrically-opposite triangular flexible flap portions integral with and extending from the cylindrical end portion, each flexible flap portion having a free apical end; securing the cylindrical end of the tissue valve being secured to a native annulus in the heart, and securing the apical end of each flexible flap portion to papillary muscle of a ventricle or to a side wall of the pulmonary artery or the aorta.

5. A method according to claim 4 including securing the apical end of each flap portion to said papillary muscle or side wall by temporarily securing opposite side edges of an upper part of the flap portion to the native annulus at diametrically-opposite positions, securing the apical end of the flap portion to said papillary muscle or side wall, and releasing the upper part of the flap portion from the native annulus.

6. A method according to claim 4 including providing the tissue valve by excising a rectangular portion of tissue from the pericardium of the patient, said rectangular portion having opposite edges, securing the opposite edges together to form a cylinder with a cylindrical end and an opposite end, and removing a pair of diametrically-opposite triangular portions from the opposite end of the tissue cylinder to form said pair of diametrically-opposite triangular flap portions, and securing said cylindrical end to the native annulus.

7. A method of replacing a cardiac valve in a heart of a patient;
the method comprising providing a tissue valve consisting of flexible unsupported endocardial tissue having a bishop's miter shape with a cylindrical end portion and a pair of diametrically-opposite triangular flexible flap portions integral with and extending from the cylindrical end portion, each flexible flap portion having a free end,
and securing the apical ends of each flap portion to papillary muscle of a ventricle or to a side wall of the pulmonary artery or the aorta.

* * * * *